(12) United States Patent
Jonas et al.

(10) Patent No.: US 8,221,779 B2
(45) Date of Patent: Jul. 17, 2012

(54) COMPOSITIONS AND METHODS FOR THE DELIVERY OF POORLY WATER SOLUBLE DRUGS AND METHODS OF TREATMENT

(75) Inventors: Jeffrey M. Jonas, Bryn Mawr, PA (US); Roger A. Rajewski, Lawrence, KS (US); Bala Subramaniam, Lawrence, KS (US); Katherine F. Terranova, Overland Park, KS (US)

(73) Assignee: CritiTech, Inc.

( * ) Notice: Subject to any disclaimer, the term of this patent is extended or adjusted under 35 U.S.C. 154(b) by 626 days.

(21) Appl. No.: 12/394,833

(22) Filed: Feb. 27, 2009

(65) Prior Publication Data

US 2009/0197821 A1    Aug. 6, 2009

Related U.S. Application Data

(62) Division of application No. 10/270,854, filed on Oct. 15, 2002, now abandoned.

(60) Provisional application No. 60/329,291, filed on Oct. 15, 2001.

(51) Int. Cl.
*A61F 2/02* (2006.01)

(52) U.S. Cl. ........................................ 424/423

(58) Field of Classification Search ............ None
See application file for complete search history.

(56) References Cited

U.S. PATENT DOCUMENTS

| | | | |
|---|---|---|---|
| 4,489,055 A | 12/1984 | Couvreur et al. | |
| 5,145,684 A | 9/1992 | Liversidge et al. | |
| 5,399,363 A | 3/1995 | Liversidge et al. | |
| 5,494,683 A | 2/1996 | Liversidge et al. | |
| 5,707,634 A | 1/1998 | Schmitt | |
| 5,833,891 A | 11/1998 | Subramaniam et al. | |
| 5,834,025 A | 11/1998 | Garavilla et al. | |
| 5,858,410 A | 1/1999 | Muller et al. | |
| 5,874,029 A | 2/1999 | Subramaniam et al. | |
| 5,916,596 A * | 6/1999 | Desai et al. | 424/489 |
| 6,106,566 A * | 8/2000 | Klein | 703/27 |
| 6,106,866 A | 8/2000 | Raney | |

(Continued)

FOREIGN PATENT DOCUMENTS

EP    0949203A1    10/1999

(Continued)

OTHER PUBLICATIONS

Alberts, et al. Intraperitoneal Cisplatin Plus Intravenous Cyclophosphamide Versus Intravenous Cisplatin Plus Intravenous Cyclophosphamide for Stage III Ovarian Cancer, The New England Journal of Medicine (1996) vol. 335 No. 26, pp. 1950-1955.

(Continued)

*Primary Examiner* — Carlos Azpuru
(74) *Attorney, Agent, or Firm* — Rick Matos; Innovar, L.L.C.

(57) ABSTRACT

The present embodiment of the invention is generally directed to compositions comprising suspensions of poorly water-soluble compounds recrystallized in nanoparticulate sizes ranging from 0.1 to 5 μm. In addition, the embodiment of the invention is directed to methods for preparation and administration of these compositions to a patient for prevention and treatment of disease states. In particular, the embodiment of the invention is directed to compositions comprising suspensions of poorly water-soluble compounds, such as antimitotics and antibiotics, in nanoparticulates and methods of prevention and treatment of chronic disease states, such as cancer, by intraperitoneal and intravenous administration of such compositions.

21 Claims, 7 Drawing Sheets

U.S. PATENT DOCUMENTS

| | | | |
|---|---|---|---|
| 6,113,795 | A | 9/2000 | Subramaniam et al. |
| 6,267,989 | B1 | 7/2001 | Liversidge et al. |
| 6,268,470 | B1 | 7/2001 | Shyjan |
| 6,270,806 | B1 | 8/2001 | Liversidge et al. |
| 6,410,756 | B1 | 6/2002 | Zamir et al. |
| 6,414,014 | B1 | 7/2002 | Canetta et al. |
| 6,419,900 | B2 | 7/2002 | Placke et al. |
| 6,441,025 | B2 | 8/2002 | Li et al. |
| 6,447,796 | B1 | 9/2002 | Vook et al. |
| 2002/0000681 | A1 | 1/2002 | Gupta et al. |
| 2008/0060095 | A1 | 3/2008 | Warkentin |

FOREIGN PATENT DOCUMENTS

| | | |
|---|---|---|
| WO | WO97/31691 | 9/1997 |
| WO | WO98/14174 | 4/1998 |
| WO | WO99/00113 A1 | 1/1999 |
| WO | WO0071079 | 11/2000 |

OTHER PUBLICATIONS

Atkinson, et al., Principles of Clinical Pharmacology, Academic Press, (2001), pp. 96-98.

Dedrick, et al, Pharmacokinetic Rationale for Peritoneal Drug Administration in the Treatment of Ovarian Cancer, Cancer Treatment Reports, (1978) vol. 62, No. 31, pp. 1-11.

E. Merisko-Liversidge et al, Formulation and Antitumor Activity Evaluation of Nanocrystalline Suspensions of Poorly Soluble Anticancer Drugs, Pharmaceutical Research, vol. 13, No. 2, 1996, pp. 272-278.

C. Jacobs et al, Nanosuspensions as a New Approach for the Formulation for the Poorly Soluble Drug Tarazepide, International Journal of Pharmaceutics, 196 (2000) pp. 161-164.

Jiahui Hu et al, Nanoparticle Engineering Process for Enhancing the Dissolution Rates of Poorly Water Soluble Drugs. Drug Development and Industrial Pharmacy, vol. 30, No. 3, 2004. pp. 233-245.

J.E. Kipp. The Role of Solid Nanoparticle Technology in the Parenteral Delivery of Poorly Water-Soluble Drugs. International Journal of Pharmaceutics, 284 (2004) pp. 109-122.

Jiahui Hu et al, Nanoparticle Engineering Process for Enhancing the Dissolution Rates of Poorly Water Soluble Drugs. Drug Development and Industrial Pharmacy, vol. 30, No. 3, 2004, pp. 233-245.

* cited by examiner

US 8,221,779 B2

COMPOSITIONS AND METHODS FOR THE DELIVERY OF POORLY WATER SOLUBLE DRUGS AND METHODS OF TREATMENT

CROSS-REFERENCE TO EARLIER FILED APPLICATIONS

The present application claims the priority of and is a divisional of U.S. application Ser. No. 10/270,854, filed Oct. 15, 2002, which claims the benefit of Provisional Application No. 60/329,291, filed on Oct. 15, 2001, the entire disclosures of which is hereby incorporated by reference.

FIELD OF THE INVENTION

The present embodiment of the invention is directed generally to the prevention and treatment of disease such as neoplastic cell growth and proliferation and, more specifically, to compositions of poorly water soluble compounds, such as, antimitotics and antibiotics, and methods of delivering such compositions for the prevention and treatment of cancers and tumors.

BACKGROUND OF THE INVENTION

Cancer is one of the leading causes of death in the United States and is characterized by uncontrolled increases in abnormal or neoplastic cells that form a tumor mass and invade adjacent tissues. Malignant cells spread by way of the blood system, the lymphatic system to lymph nodes, by migration of cancer cells within the fluids of the peritoneal cavity, and to distant sites in a process known as metastasis.

Numerous compounds are known which are useful in the prevention and treatment of various types of cancer. In order to effectively deliver these compounds by intravenous administration, it is generally preferred that the compounds be in solution to avoid or reduce the risk of blood clotting or other adverse effects that could result if the compounds were delivered in particulate form. Unfortunately, many of these compounds have poor solubility in water, the preferred solvent, and must be delivered using solvents which can cause adverse patient reactions that must in turn be prevented or controlled through the administration of other compounds. For example, paclitaxel is a known inhibitor of cell division or mitosis and is widely used in the treatment of ovarian, breast, lung, esophageal, bladder, head and neck cancers. Paclitaxel is a natural product originally purified from the bark of yew trees, but now obtained by semisynthesis from 10-desacetylbaccatin, a precursor purified from yew leaves. Paclitaxel, however, is poorly water soluble and is conventionally solubilized in Cremophor EL, a formulation comprising 50% ethyl alcohol and 50% polyethoxylated castor oil. Cremophor EL is believed to result in histamine release in certain individuals and patients receiving paclitaxel in that delivery method must normally be protected with a histamine $H_1$-receptor antagonist, an $H_2$-receptor antagonist and a corticosteroid to prevent severe hypersensitivity reactions. Other compounds cannot be effectively administered because they are not soluble in any known solvent that can be tolerated by patients in need of cancer prevention or treatment. As a result, these anti-cancer agents are unavailable for use in cancer prevention or treatment using conventional methods of administration.

While anti-cancer compounds are commonly administered by intravenous injection to patients in need of treatment, it is also known to inject cisplatin and carboplatin into the peritoneal cavity. A comparative study of intravenous versus intraperitoneal administration of cisplatin has been published by Alberts, et al. in the New England Journal of Medicine, 335, 1950-1955 (1996). Dedrick, et al., have published a pharmacokinetic rationale for the advantage of intraperitoneal versus intravenous administration of cisplatin in Cancer Treatment Reports, 62, 1-11 (1978). Similarly, intraperitoneal delivery of cisplatin as an infusion is discussed in Principles of Clinical Pharmacology (Atkinson, et al., Academic Press 2001). To date, however, there do not appear to be any published reports of intraperitoneal delivery of suspensions of poorly water-soluble anticancer compounds.

SUMMARY OF THE INVENTION

A composition comprising nanoparticulates of at least one antimitotic drug, where the nanoparticulates have a particle size from 0.1 micrometer to 5 micrometers.

A composition comprising nanoparticulates of at least one antimitotic drug, where the nanoparticulates have a particle size from 0.1 micrometer to 5 micrometers in a suspension medium.

A method of administering intraperitoneally a composition comprising nanoparticulates of at least one antimitotic drug in a suspension medium, where the nanoparticulates have a particle size from 0.1 micrometer to 5 micrometers.

A method of administering intravenously a composition comprising nanoparticulates of at least one antimitotic drug in a suspension medium, where the nanoparticulates have a particle size from 0.1 micrometer to 5 micrometers.

A composition comprising nanoparticulates of paclitaxel, where the nanoparticulates have a particle size from 0.1 micrometer to 5 micrometers.

A composition comprising nanoparticulates of paclitaxel, where the nanoparticulates have a particle size from 0.1 micrometer to 5 micrometers in a suspension medium.

A method of administering intraperitoneally a composition comprising nanoparticulates of paclitaxel in a suspension medium, where the nanoparticulates have a particle size from 0.1 micrometer to 5 micrometers.

A method of administering intravenously a composition comprising nanoparticulates of paclitaxel in a suspension medium, where the nanoparticulates have a particle size from 0.1 micrometer to 5 micrometers.

A composition comprising nanoparticulates of at least one antibiotic drug, where the nanoparticulates have a particle size from 0.1 micrometer to 5 micrometers.

A composition comprising nanoparticulates of at least one antibiotic drug, where the nanoparticulates have a particle size from 0.1 micrometer to 5 micrometers in a suspension medium.

A method of administering intraperitoneally a composition comprising nanoparticulates of at least one antibiotic drug in a suspension medium, where the nanoparticulates have a particle size from 0.1 micrometer to 5 micrometers.

A method of administering intravenously a composition comprising nanoparticulates of at least one antibiotic drug in a suspension medium, where the nanoparticulates have a particle size from 0.1 micrometer to 5 micrometers.

BRIEF DESCRIPTION OF THE FIGURES

The present embodiment of the invention is described in detail below with reference to the attached drawing figures, wherein.

DETAILED DESCRIPTION OF THE INVENTION

Figure 1:
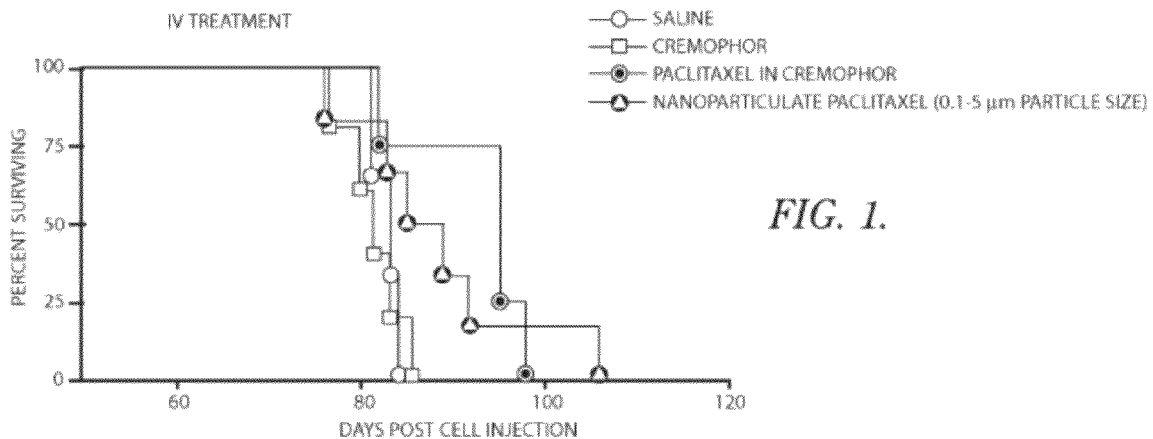
FIG. 1 is a graph illustrating the results from a study of cancer bearing mice treated with nanoparticulate paclitaxel administered intravenously compared with controls and paclitaxel in Cremophor solution.

The present embodiment of the invention is generally directed to compositions comprising suspensions of poorly water soluble compounds recrystallized in nanoparticulate sizes ranging from 0.1 to 5 µm, and more preferably from 0.4 to 2 µm. In addition, the embodiment of the invention is directed to methods for preparation and administration of these compositions to a patient for prevention and treatment of disease states. In particular, the embodiment of the invention is directed to compositions comprising suspensions of poorly water-soluble compounds, such as antimitotics and antibiotics, in nanoparticulates and methods of prevention and treatment of chronic disease states, such as cancer, by intraperitoneal and intravenous administration of such compositions.

Various processes are disclosed in U.S. Pat. Nos. 5,833,891 and 6,113,795, which are incorporated by reference herein in their entireties, for producing particle sizes as small as 0.1 to 10 µm for compounds. Because particles that are smaller than one to two microns can pass through the smallest capillaries in the human body, it is desirable to determine whether suspensions of small size particles of anti-cancer compounds could be injected into the blood stream and produce a therapeutic effect without causing blood clotting or other undesirable side effects as a result of aggregation of the small particles into larger particles or aggregation of platelets on the surface of the particles.

Antimitotics as used herein, include, but are not limited to: paclitaxel; derivatives of paclitaxel; taxanes; epithilones, Vinca alkaloids, such as vinblastine, vincristine, vindesine, vinorelbine; camptothecin analogs; and epipodophyllotoxins, such as etoposide and teniposide. Poorly water-soluble antibiotics, include, but are not limited to, actinomycin D, mitomycin, daunorubicin, doxorubicin and idarubicin.

Poorly water soluble compounds, as used herein, are compounds that include: insoluble compounds that have <0.01 mg/ml solubility, very slightly soluble compounds that have 0.1-1 mg/ml solubility, slightly soluble compounds that have 1-10 mg/ml solubility and sparingly soluble compounds that have 10-33 mg/ml solubility. The compositions of the present embodiment of the invention may include other pharmaceutically acceptable ingredients, excipients and adjuvants.

The nanoparticulate intraperitoneal delivery described in this application may ameliorate some of the side effects of administering a poorly water-soluble drug by allowing a lower dose to be delivered over a long period of time.

EXAMPLE 1

In this example, using the process described in U.S. Pat. Nos. 5,833,891 and 6,113,795, paclitaxel was recrystallized to an average particle size of about 700 nanometers and a particle size distribution such that greater than 95% of the particles were below one micron in size as determined by aerodynamic Time-of-Flight particle sizing. Four groups of mice that had previously been injected with cancerous cells and had developed ovarian cancer were treated with one of the following: 1) a phosphate buffered saline alone, used as a control 2) a Cremophor EL solution alone, used as a control, 3) paclitaxel in Cremophor EL solution injected by intravenous (IV) administration, or 4) nanoparticulate paclitaxel suspended in phosphate buffered saline and injected by IV administration. The mice were injected with the treatment, comparative and control compositions on the fiftieth day after inoculation with cancer cells. Four doses of the compositions were injected every other day.

The saline control group survived for a maximum of 110 days post cancer cell injection and the Cremophor control group survived for a maximum of 113 days post cancer cell injection. By day 125, the last of the nanoparticulate paclitaxel group expired and the group injected with paclitaxel in Cremophor was 80% expired. There appears to be no statistical difference in overall survival of mice treated by IV with nanoparticulate paclitaxel in suspension and paclitaxel in Cremophor solution. The results of the IV injection study are shown in FIG. 1.

Notably, the mice survived the direct IV injection of the suspension of nanoparticulate paclitaxel in phosphate buffered saline without the need to add anticlotting agents such as heparin or agents such as surfactants or emulsifiers to prevent aggregation of the particles. While the preferred formulations would include these additional ingredients to further reduce the opportunity for clotting, the nanoparticulate paclitaxel did not appear to cause blockage or infarct of fine capillaries. Surprisingly, it was determined that IV injection of the nanoparticulate suspension of paclitaxel was as effective as the solution of paclitaxel in Cremophor EL in lengthening the survival time for mice inoculated with cancer cells. As a result, it may be possible to deliver a suspension of nanoparticulate paclitaxel intravenously with the same therapeutic effect as a solution of paclitaxel in Cremophor, but without the adverse effects of Cremophor.

EXAMPLE 2

In this example, using the process described in U.S. Pat. Nos. 5,833,891 and 6,113,795, paclitaxel was recrystallized to an average particle size of about 700 nanometers and a particle size distribution such that greater than 95% of the particles were below one micron in size as determined by aerodynamic Time-Of-Flight particle sizing. Eight groups of mice that had previously been injected with cancerous cells and had developed ovarian cancer were treated with one of the following: 1) a phosphate buffered saline alone, used as a control; 2) a Cremophor EL solution alone, used as a control; 3) paclitaxel in Cremophor EL solution, 12 mg/kg administered intraperitoneal administration; 4) paclitaxel in Cremophor EL solution, 18 mg/kg injected by IP administration; 5) paclitaxel in Cremophor solution, 36 mg/kg injected by IP administration; 6) nanoparticulate paclitaxel suspended in phosphate buffered saline, 18 mg/kg administered intraperitoneally; 7) nanoparticulate paclitaxel suspended in phosphate buffered saline, 36 mg/kg administered intraperitoneally; or 8) nanoparticulate paclitaxel suspended in phosphate buffered saline, 48 mg/kg administered intraperitoneally. The mice were injected with the treatment, comparative, and control compositions on the fiftieth day after inoculation with cancer cells. Four doses of the compositions were injected every other day.

Figure 2:
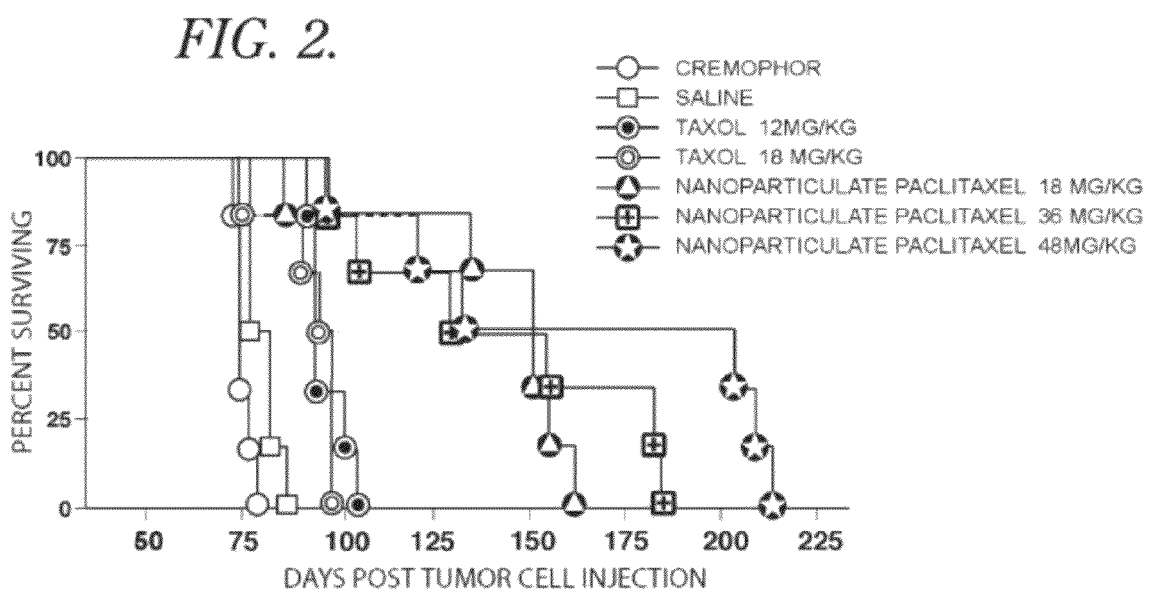
FIG. 2 is a graph illustrating the results from a study of cancer bearing mice treated with nanoparticulates of paclitaxel administered intraperitoneally compared with controls and paclitaxel in Cremophor solution.

The longest surviving Cremophor control mouse lasted until 79 days post cancer cell injection. For the phosphate buffered saline control group, the last member of the control group expired on day 87. For the paclitaxel in Cremophor group, the last mouse survived up to day 99 for the 18 mg/kg dose and day 105 for the 12 mg/kg dose. The 36 mg/kg dosage group did not survive treatment. For the nanoparticulate paclitaxel in phosphate buffered saline group, administered intraperitoneally, the last mouse survived up to day 162 for the 18 mg/kg dose, day 181 for the 36 mg/kg dose, and day 220 for the 48 mg/kg dose. This represents a significant increase in survival in comparison to IV administration. The results of the intraperitoneal injection study are shown in FIG. 2.

Figure 4:
FIG. 4 is a photograph of the body wall of a cancer bearing mouse treated with the saline control.
Figure 5:
FIG. 5 is a photograph of the body wall of a cancer bearing mouse treated with 48 mg/kg of nanoparticulates of paclitaxel in suspension administered intraperitoneally.

It was determined that intraperitoneal injection of the suspension of paclitaxel nanoparticulates significantly lengthened the survival time of the mice in comparison to the intraperitoneal injection of solubilized paclitaxel in Cremophor. Further, as can be seen from FIG. 4-FIG. 13, the mouse treated with nanoparticulate paclitaxel, administered intraperitoneally, developed fewer cancerous tumors and spreading of the cancer was less aggressive than the cancer in the saline control mouse. FIG. 4 is a photograph of the body wall of a mouse treated with the saline control showing numerous cancerous tumors. FIG. 5 shows the body wall of a mouse treated with 48 mg/kg of nanoparticulates of paclitaxel in suspension administered peritoneally and shows few, if any, cancerous tumors.

Figure 6:
FIG. 6 is a photograph of the diaphragm of a cancer bearing mouse treated with the saline control.
Figure 7:
FIG. 7 is a photograph of the diaphragm of a cancer bearing mouse treated with 48 mg/kg of nanoparticulates of paclitaxel in suspension administered intraperitoneally.
Figure 8:
FIG. 8 is a photograph of an external view of a cancer bearing mouse treated with the saline control.
Figure 9:
FIG. 9 is a photograph of an external view of a cancer bearing mouse treated with 48 mg/kg of nanoparticulates of paclitaxel in suspension administered intraperitoneally.
Figure 10:
FIG. 10 is a photograph of the kidneys of a cancer bearing mouse treated with the saline control.
Figure 11:
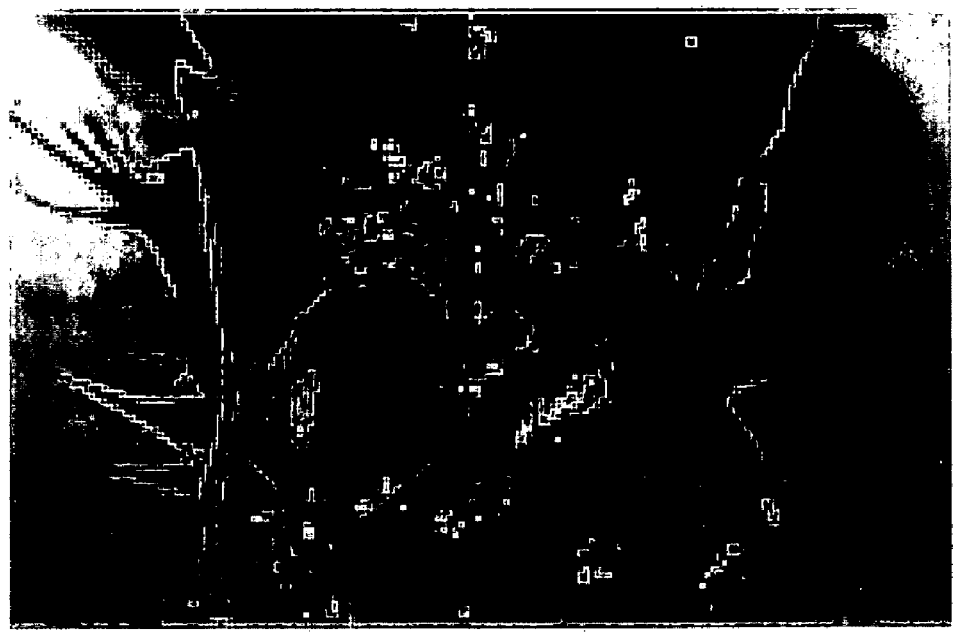
FIG. 11 is a photograph of the kidneys of a cancer bearing mouse treated with 48 mg/kg of nanoparticulates of paclitaxel in suspension administered intraperitoneally.
Figure 12:
FIG. 12 is a photograph of the peritoneal organs of a cancer bearing mouse treated with the saline control.
Figure 13:
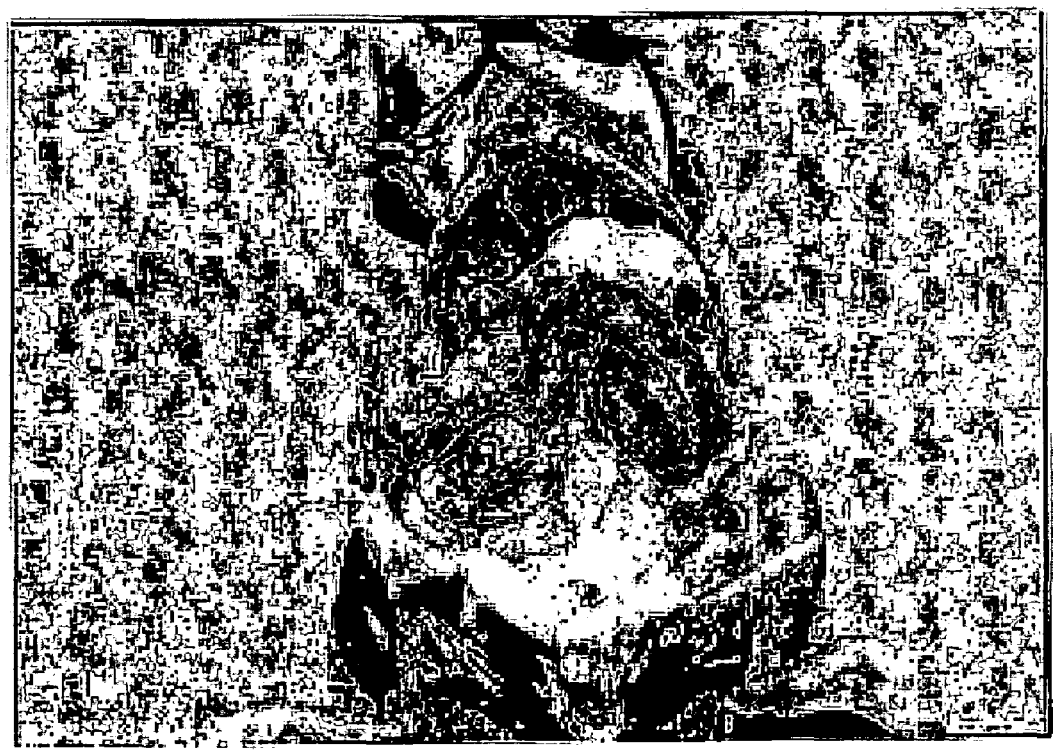
FIG. 13 is a photograph of the peritoneal organs of a cancer bearing mouse treated with 48 mg/kg of nanoparticulates of paclitaxel in suspension administered intraperitoneally.

The diaphragm of a mouse treated with the saline control is depicted in FIG. 6, where numerous cancerous tumors can be seen. The diaphragm of a mouse treated with 48 mg/kg of nanoparticulates of paclitaxel in suspension administered peritoneally, as shown in FIG. 7, does not show the same proliferation of cancerous tumors. FIG. 8 is a photograph of an external view of a mouse treated with the saline control where abdominal cavity of the mouse is distended from the spreading of the cancer and the accumulation of ascetic fluids. On the other hand, the external view of the mouse treated with nanoparticulates of paclitaxel in FIG. 9 is normal. FIG. 10 is a photograph of the kidneys with numerous cancerous tumors of a mouse treated with the saline control. FIG. 11 is a photograph of the healthy kidneys of a mouse treated with nanoparticulates of paclitaxel in suspension administered peritoneally. FIG. 12 is a photograph of the cancerous growths on the peritoneal organs of a mouse treated with the saline control, while FIG. 13 does not show any cancerous growths on the peritoneal organs of a mouse treated with nanoparticulates of paclitaxel.

EXAMPLE 3

In this example, nine groups of mice that had previously been injected with cancerous cells and had developed ovarian cancer were treated with one of the following: 1) a phosphate buffered saline alone, used as a control; 2) a Cremophor EL solution alone, used as a control; 3) paclitaxel in Cremophor EL solution, 18 mg/kg injected by IP administration; 4) macroparticulate paclitaxel, 18 mg/kg administered intraperitoneally; 5) macroparticulate paclitaxel, suspended in phosphate buffered saline, 36 mg/kg administered peritoneally; 6) macroparticulate paclitaxel suspended in phosphate buffered saline, 48 mg/kg administered intraperitoneally; 7) nanoparticulate paclitaxel suspended in phosphate buffered saline, 18 mg/kg administered intraperitoneally; 8) nanoparticulate paclitaxel suspended in phosphate buffered saline, 36 mg/kg administered intraperitoneally; or 9) nanoparticulate paclitaxel suspended in phosphate buffered saline, 48 mg/kg administered intraperitoneally. The mice were injected with the treatment, comparative, and control compositions on the fiftieth day after inoculation with cancer cells. Four doses of the compositions were injected every other day.

Figure 3:
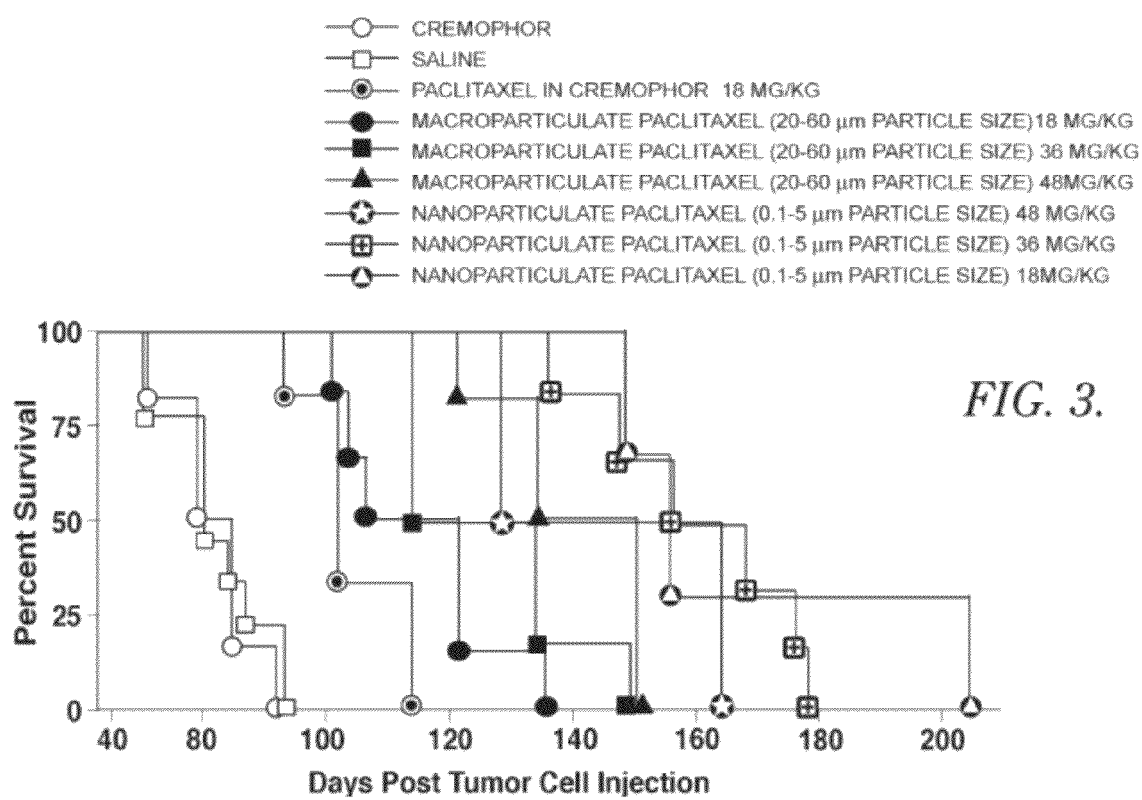
FIG. 3 is a graph illustrating the results from a study of cancer bearing mice treated with macroparticulates of paclitaxel, 20 to 60 microns in size, administered intraperitoneally compared with controls, paclitaxel in Cremophor solution and nanoparticulate paclitaxel administered intraperitoneally.

The longest surviving Cremophor control mouse lasted until 92 days post cancer cell injection. For the phosphate buffered saline control group, the last member of the control group survived until day 93. For the paclitaxel in Cremophor group, the maximal survival time was to day 115. For the macroparticulate (20-60 μm particle size) paclitaxel in phosphate buffer saline group, the maximal survival time was 137 days for the 18 mg/kg dose, 150 days for the 36 mg/kg dose and 151 days for the 48 mg/kg dose. For the nanoparticulate paclitaxel in phosphate buffer saline, the last member of the group expired on day 162 for the 48 mg/kg dosage group, day 179 for the 36 mg/kg dosage group and day 205 for the 18 mg/kg dosage group. The survival time for mice treated with macroparticulate paclitaxel was greater than the survival time of mice treated with paclitaxel in Cremophor. However, the mice treated with nanoparticulate paclitaxel had the longest survival time. The results of this intraperitoneal injection study are shown in FIG. 3.

The present embodiment of the invention has been described in relation to particular embodiments which are intended in all respects to be illustrative rather than restrictive. Alternative embodiments will become apparent to those skilled in the art to which the present invention pertains without departing from its scope. From the foregoing, it will be seen that this invention is one well adapted to attain all the ends and objects hereinabove set forth together with other advantages which are obvious and which are inherent to the compositions and methods of making and using such compositions herein disclosed. Since many possible embodiments may be made of the invention without departing from the scope thereof, it is to be understood that all matter herein set forth or shown in the accompanying drawing is to be interpreted as illustrative and not in a limiting sense.

The invention claimed is:

1. A method of treating neoplastic cell growth and proliferation in a subject in need thereof comprising:
    a) providing an injectable composition consisting of a liquid carrier and microparticles, the microparticles consisting of an antimitotic drug, or a poorly water soluble antibiotic, wherein the microparticles have a particle size of 0.1 to 5 micrometers; and b) administering an effective amount of the composition intraperitoneally to the subject.

2. The method of claim 1, wherein the composition is a suspension.

3. The method of claim 2, wherein the liquid carrier is an aqueous liquid carrier.

4. A method of treating neoplastic cell growth and proliferation in a subject in need thereof comprising:
    a) providing an injectable suspension composition consisting of: an aqueous liquid carrier, and microparticles, the microparticles consisting of an antimitotic, or a poorly water soluble antibiotic drug, wherein the microparticles have a particle size of 0.1 to 5 micrometers; and
    b) administering an effective amount of the composition intraperitoneally to the subject;
    c) wherein the composition provides a greater therapeutic benefit than a control composition consisting of: the same amount of the same antimitotic compound or poorly water soluble antibiotic, and a liquid carrier consisting of ethyl alcohol 50% and polyethoxylated castor oil 50%.

5. The method of claim 3 or 4, wherein the aqueous liquid carrier is saline.

6. The method of claim 5, wherein the aqueous liquid carrier is phosphate buffered saline.

7. The method of claim 1 or 4, wherein:
    a) the antimitotic drug is selected from the group consisting of paclitaxel, derivatives of paclitaxel, taxanes, epithilones, Vinca alkaloids, camptothecin analogs, and epipodophyllotoxins; or
    b) the poorly water soluble antibiotic is selected from the group consisting of actinomycin D, mitomycin, daunorubicin, doxorubicin and idarubicin.

8. A method of treating neoplastic cell growth and proliferation in a subject in need thereof comprising:
    a) providing an injectable composition consisting of a liquid carrier and microparticles consisting of an epipodophyllotoxin or Vinca alkaloid, the microparticles having a particle size of 0.1 to 5 micrometers, wherein the epipodophyllotoxin is selected from the group consisting of etoposide and teniposide, or the Vinca alkaloid is selected from the group consisting of vinblastine, vincristine, vindesine or vinorelbine; and
    b) administering an effective amount of the composition intraperitoneally to the subject.

9. A method of treating neoplastic cell growth and proliferation in a subject in need thereof comprising:
    a) providing an injectable composition consisting of a liquid carrier and microparticles, the microparticles consisting of an antimitotic drug, or a poorly water soluble antibiotic, wherein the microparticles have a particle size of 0.1 to 5 micrometers, wherein the composition further contains anti-clotting agent or surfactant; and
    b) administering an effective amount of the composition intraperitoneally to the subject.

10. The method of claim 1 or 4, wherein the microparticles having a particle size of 0.4 to 2 micrometers.

11. The method of claim 1, wherein the composition provides a greater therapeutic benefit than a control solution composition consisting of: the same amount of the same antimitotic compound or poorly water soluble antibiotic, and a liquid carrier consisting of ethyl alcohol 50% and polyethoxylated castor oil 50%.

12. The method of claim 4 or 11, wherein the greater therapeutic benefit is increased survival time for the subject, a decrease in the number of cancerous tumors developed by the subject, or less spreading of the cancer in the subject.

13. The method of claim 4 or 11, where the greater therapeutic benefit is achieved at a composition and dose that are considered non-toxic for the subject.

14. The method of claim 4 or 11, wherein the neoplastic cell growth and proliferation is cancer or tumor.

15. The method of claim 14, wherein the neoplastic cell growth and proliferation is selected from the group consisting of ovarian cancer, breast cancer, lung cancer, esophageal cancer, bladder cancer, head cancer and neck cancer.

16. The method of claim 1 or 4, wherein the composition is administered several times per day.

17. The method of claim 1 or 4, wherein the composition is administered every other day.

18. The method of claim 1 or 4, wherein the composition is administered four times per day every other day for a period of five days.

19. The method of claim 1 or 4, wherein the effective amount of composition is 12 to 48 mg of antimitotic drug per kg of subject.

20. A method of treating neoplastic cell growth and proliferation in a subject in need thereof comprising:
    a) providing an injectable suspension composition consisting of: an aqueous liquid carrier, and microparticles consisting of an epipodophyllotoxin or Vinca alkaloid, the microparticles drug having a particle size of 0.1 to 5 micrometers, wherein the epipodophyllotoxin is selected from the group consisting of etoposide and teniposide, or the Vinca alkaloid is selected from the group consisting of vinblastine, vincristine, vindesine or vinorelbine; and
    b) administering an effective amount of the composition intraperitoneally to the subject;
    c) wherein the composition provides a greater therapeutic benefit than a control composition consisting of: the same amount of the same antimitotic compound or poorly water soluble antibiotic, and a liquid carrier consisting of ethyl alcohol 50% and polyethoxylated castor oil 50%.

21. A method of treating neoplastic cell growth and proliferation in a subject in need thereof comprising:
    a) providing an injectable suspension composition consisting of: an aqueous liquid carrier, and microparticles, the microparticles consisting of an antimitotic, or a poorly water soluble antibiotic drug, wherein the microparticles have a particle size of 0.1 to 5 micrometers and wherein the composition further contains anti-clotting agent or surfactant; and
    b) administering an effective amount of the composition intraperitoneally to the subject;
    c) wherein the composition provides a greater therapeutic benefit than a control composition consisting of: the same amount of the same antimitotic compound or poorly water soluble antibiotic, and a liquid carrier consisting of ethyl alcohol 50% and polyethoxylated castor oil 50%.

* * * * *